United States Patent [19]
Errico et al.

[11] Patent Number: 5,531,746
[45] Date of Patent: *Jul. 2, 1996

[54] POSTERIOR SPINAL POLYAXIAL LOCKING LATERAL MASS SCREW PLATE ASSEMBLY

[75] Inventors: Joseph P. Errico, Hempstead, N.Y.; Thomas J. Errico, Summit; James Ralph, Oakland, both of N.J.

[73] Assignee: Fastenetix, L.L.C., Summit, N.J.

[ * ] Notice: The term of this patent shall not extend beyond the expiration date of Pat. No. 5,520,690.

[21] Appl. No.: 446,222

[22] Filed: May 22, 1995

Related U.S. Application Data

[63] Continuation-in-part of Ser. No. 421,087, Apr. 13, 1995.

[51] Int. Cl.$^6$ ................................................. A61B 17/70
[52] U.S. Cl. ................................ 606/61; 606/70; 606/73
[58] Field of Search ................................. 606/61, 69, 70, 606/71, 72, 73, 75, 76, 104; 623/17, 16

[56] References Cited

U.S. PATENT DOCUMENTS

| | | | |
|---|---|---|---|
| 5,053,036 | 10/1991 | Perren et al. | 606/69 |
| 5,057,111 | 10/1991 | Park | 606/69 |
| 5,147,361 | 9/1992 | Ojima et al. | 606/61 |
| 5,180,381 | 1/1993 | Aust et al. | 606/61 |
| 5,269,784 | 12/1993 | Mast | 606/69 |
| 5,324,290 | 6/1994 | Zdeblick et al. | 606/61 |
| 5,429,639 | 7/1995 | Judet | 606/61 |

FOREIGN PATENT DOCUMENTS

| | | | |
|---|---|---|---|
| 9416634 | 8/1994 | WIPO | 606/69 |

OTHER PUBLICATIONS

"Cervi–Lok Cervical Fixation System", Spinetech, Inc., 980 East Hennepin Ave., Minneapolis, Minn 55414, 1994 Author unknown.

"System Overview—Axis Fixation System", Sofamor Danek, 1800 Pyramid Place, Memphis Tenn 38132, 1994 Author unkown.

"Surgical Technique—Orion Anterior Cervical Plate System", Sofamor Danek, 1800 Pyramid Place, Memphis Tenn 38132, 1994 Author unknown.

"Surgical Technique—ZPlate–ATL Anterior Fixation System", Sofamor Danek, 1800 Pyramid Place, Memphis Tenn 38132, 1994 Author unknown.

*Primary Examiner*—Guy Tucker
*Attorney, Agent, or Firm*—J. P. Errico

[57] ABSTRACT

The present invention is a polyaxial lateral mass locking screw plate assembly for immobilization of vertebral bones, via fixation to surfaces thereof. In one embodiment the invention includes a narrow elongate plate having a plurality of holes, which in one variation are threaded, into which holes coupling elements may be inserted, or correspondingly screwed. The coupling elements have a cylindrical exterior, and have an semi-spherical interior volume into which the semi-spherical head of a bone screw may be inserted, and therein polyaxially mounted. In one variation the coupling element is a ⅞ths ring including a single axial slot. In another variation the coupling element includes a plurality of slots in its lower portion. In either variation insertion of a coupling element into a corresponding hole causes the interior volume to be crush locked to the head of the screw. In a second embodiment, the present invention includes a similar plate, having holes which are, however, threaded part of the way through the plate. In this embodiment, the bottom portion of the holes of the plate, additionally, have a curved interior surface which forms an annular lip for supporting a semi-spherical head portion of a bone screw. The coupling element of this embodiment is a short threaded cylindrical piece, having a concave bottom which locks the screw into the hole. Variations of each embodiment have means associated with the holes and/or the coupling element for locking the angle of the screw to the plate.

7 Claims, 8 Drawing Sheets

POSTERIOR SPINAL POLYAXIAL LOCKING LATERAL MASS SCREW PLATE ASSEMBLY

CROSS-REFERENCE TO RELATED APPLICATION

This application is a continuation-in-part of U.S. Ser. No. 08/421,087, filed Apr. 13, 1995, "Anterior spinal Polyaxial Locking Screw Plate Assembly" (Attorney Docket F-101) still pending.

BACKGROUND OF THE INVENTION

1. Field of the Invention

This invention relates generally to a posterior cervical implant assembly for holding adjacent vertebral bones immobilized via fixation to the lateral masses. More particularly, this invention relates to a novel assembly of bone screws and plates for use in surgical procedures for stabilizing the relative motion of, or permanently immobilizing, vertebral bodies in the cervical spine, wherein the screws form a polyaxial coupling of the plate to the bone, and which coupling provides a locking of the screws to the plate through a wide range of entrance angulation.

2. Description of the Prior Art

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic and lumbar spine. For the purposes of this disclosure, however, the word spine shall refer only to the cervical region.

Figure 1:
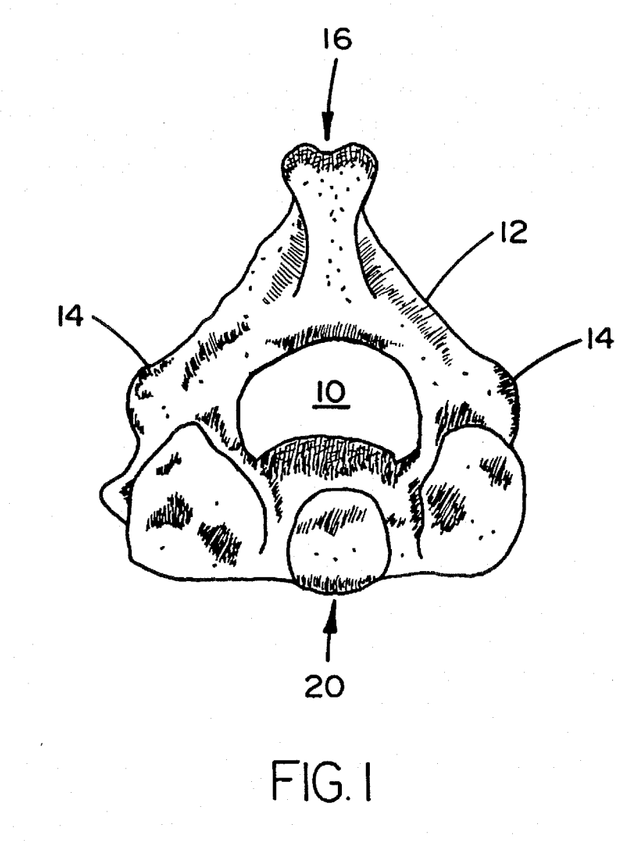
FIG. 1 is a top view of a cervical vertebra, the stabilization of which the present invention is directed.
Figure 2:
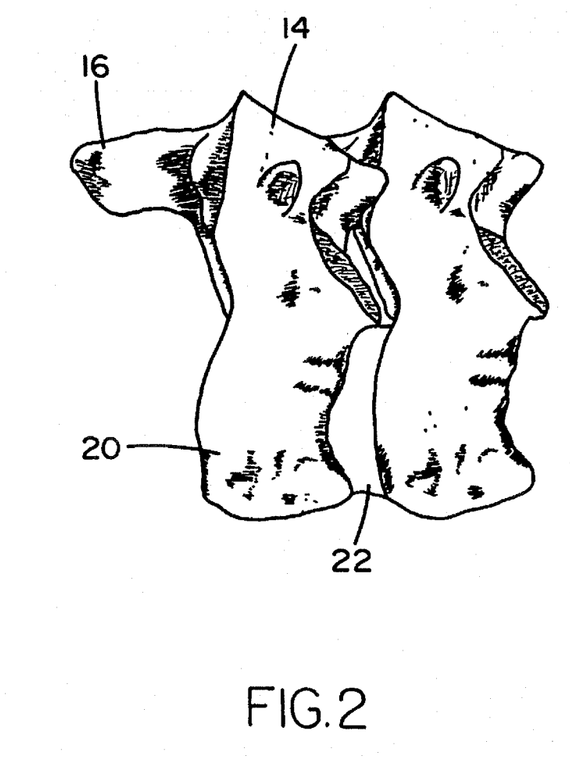
FIG. 2 is a side view of sequentially aligned cervical vertebrae.

Referring now to FIGS. 1 and 2, a typical cervical body is shown in a top view, and a pair of cervical bones and the interspecing disc are shown in a side view. The spinal cord is housed in the central canal 10, protected from the posterior side by a shell of bone called the lamina 12. The lamina 12 includes a rearwardly and downwardly extending portion called the spinous process 16, and laterally extending bulk structures, correspondingly referred to as the lateral masses 14. The anterior portion of the spine comprises a set of generally cylindrically shaped bones which are stacked one on top of the other. These portions of the vertebrae are referred to as the vertebral bodies 20, and are each separated from the other by the intervertebral discs 22. The lateral masses 14 comprise bone bridges which couple the anterior vertebral body 20 to the corresponding lamina 12.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction. The most flexible of all the regions of the spinal column is the cervical spine.

Genetic or developmental irregularities, trauma, chronic stress, tumors, and disease are a few of the causes which can result in spinal pathologies for which permanent immobilization of multiple vertebrae may be necessary. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, as well as the individual variations in anatomy, determine the appropriate surgical protocol and implantation assembly. The use of screw plate assemblies (lateral mass plates) for stabilization and immobilization of the cervical spine is, however, common. A lateral mass plate is a narrow elongate plate having a series of spaced through holes which screws may be inserted to fix the plate to the bones. A pair of lateral mass plates are placed across the lateral posterior surfaces of a set of sequential cervical bones and are secured to the bone with screws, thereby preventing the bones from moving relative to one another in either the vertical or horizontal planes.

Because the spine is routinely subject to high loads which cycle during movement, one of the primary concerns of physicians performing spinal implantation surgeries, as well as of the patients in whom the implants are placed, is the risk of screw pull-out. Screw pull-out occurs when the cylindrical portion of the bone which surrounds the inserted screw fails. A bone screw which is implanted perpendicular to the plate is particularly weak because the region of the bone which must fail for pull-out to occur is only as large as the outer diameter of the screw threads. It has been found that for pull-out to occur for screws which are inserted into the bone at an angle with respect to the plate, the amount of bone which must fail increases substantially as compared with screws which are implanted perpendicularly with respect to the plate. It has, therefore, been an object of those in the art to provide a pair of lateral mass screw plate assembly which permits the screws to be entered into the lateral masses at angles other than 90 degrees.

An additional concern with screws being implanted in the lateral masses of the cervical spine, is that their are sensitive and/or important structures adjacent to the masses, which, because of their proximity to the implant, may be damaged by insertion or dislocation of screws. In the cervical spine, the vertebral arteries are disposed medially beneath the lateral masses and comprise critical structures which cannot be compromised. In addition, the facet joints which provide natural coupling of sequential bones together must also be avoided it possible. Avoidance of these bodies has been a critical and ongoing concern with respect to posterior screw insertion. Lateral mass plates of the prior art have provided little in the way of reasonable or practical solutions for ensuring proper screw insertion.

Lateral mass screw plate assemblies necessarily include a plurality of screws which are inserted through a single plate. If a single screw loosens with respect to the surrounding bone into which it has been inserted, loss of fixation occurs and possible neurological repercussions may result. Unfortunately, as the screws of the prior art have included no means to prevent screws from "backing out" of the holes once they have loosened. It has, therefore, been a goal of those in the art to minimize the risk of screw pull-out which happens by bone failure followed by cyclical force induced back-out.

While the preceding discussion has specifically focused on cervical lateral mass screw plate systems and the concerns associated therewith, similar concerns apply to the art of posterior vertebral immobilization viw screw plate systems which are presently available in the thoracic and lumbar spine as well.

It is therefore, a principal object of the present invention to provide a new and novel cervical lateral mass screw plate design having a polyaxial coupling of the screw to the plate, whereby a single plate is compatible with a wide range of screw-in angles.

It is also, therefore, an object of the present invention to provide a screw plate design which provides the surgeon with the greatest freedom to choose the most desirable angle to direct the bone screw, so as to avoid critical structures in the cervical spine.

It is also an object of the present invention to provide a spinal insert assembly which is more sturdy and more versatile than previous designs.

It is also a principal object of the present invention to provide an orthopedic screw plate assembly which has a simple and effective locking mechanism for locking the bone screw to the plate.

It is also, therefore, an object of the present invention to provide a lateral mass screw plate assembly which resists screw pull-out failure by preventing screw back-out resulting from screw-bone failure coupled with kinesthetic force cycling.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a locking polyaxial lateral mass screw plate assembly for use in stabilizing and immobilizing vertebral bodies along the posterior surface thereof. The assembly comprises a plate having a set of through holes, which may be threaded and/or angled with respect to the plane of the plate, bone screws having a semi-spherical top portion, and a coupling element. The coupling element which may to include a corresponding external threading, or a taper crush locking axial slot for insertion and locking into the holes of the plate. The coupling element further includes an interior and/or lower surface for compressing and holding the semi-spherical top portion of the bone screw.

The present invention has a variety of embodiments, the first of which is summarized hereinbelow. The plate is a narrow, elongate, planar element, preferably constructed of a biocompatable and structurally durable metal having a generally rectangular shape with rounded corners. The plate is, further, contoured to match the small positive angle curvature of the posterior cervical spine to which it is secured. There are a plurality of threaded holes disposed along the elongate axis of the plate, which extend through the plane of the plate, positioned so that they are aligned with the lateral masses of sequential in which the plate is to be attached. The holes may be angled with respect to the perpendicular axis of the plane of the plate. This provides a natural bias toward angling the screws outward with respect to the spinal canal. There is substantial uniformity in the spacing distances between sequential lateral masses in the cervical spine across a large spectrum of human adults. The threading and shaft portion of the bone screws may be of a variety of standard designs, or a particular design which may be found more secure than the standard ones. The head, however, is not standard in that it comprises a semi-spherical section.

For the purposes of inserting the screw into the bone, the head comprises a recessed region such as a slot, phillips, star, or hexagonal recesses which are ideally suited for mating to an appropriate screwdriving tool. The recess, however, shall not alter the exterior radially semi-spherical shape of the head.

The coupling element comprises a socket for holding the ball head of the screw, and an exterior threading which mates with the threaded holes of the plate. In one variation the entire coupling element includes an axial slot (the coupling element, therefore, comprises a so-called ⅞ths locking ring) which is forced closed upon insertion into the hole in the plate, thereby locking the ball to the coupling element. In another variation, only the socket portion includes a slot (preferably a plurality of slots) for locking the ball to the coupling element. In both variations it is preferable for the coupling elements to be tapered so that insertion into the hole locks the ball to the coupling elements.

The first step in the process of implanting this embodiment of the invention is to position the plate against the lateral masses in the porterior cervical spine and to align the entry points for the screws. The next step is to pre-drill the holes into the bones at the desired angle for ideal screw insertion. With the plate in place, the screws may now be inserted through the holes in the lateral masses.

The coupling element must either provide a recess which may be positioned co-linearly with the recess in the screw head for screwing in the screw, or it must be partially open so that the screw and coupling element may be manipulated easily so that the recess in the head of the screw is accessible. In all variations, once the screw has been fully inserted into the bone, at the desired angle, the coupling element, via its rotationally free mating of the socket to the inserted screw, is realigned so that it may be threadably locked down into the plate. Screwing down the coupling element provides a secure prevention against screw back-out, as well as locking the screw at the preferred non-perpendicular angulation with respect to the plate.

In an alternative and/or preferred variation of this embodiment the threaded holes of the plate element are also tapered. In this variation screwing the coupling element into the tapered holes in the plate, has the effect of applying a radial force to the slotted socket portion and/or to the axial slot of the entire coupling element. This circumferential reduction has the desirable effect of locking the screw at the insertion angle.

Another embodiment of the present invention comprises a plate, similar to the one described above, in which the holes are threaded only partially through the plate. The unthreaded portion of the hole includes an annular curved lip at the bottom thereof, which forms a support which is ideally suited for supporting the semi-spherical top of the screw while simultaneously permitting rotational motion whereby the entrance angle of the screw may be varied through a wide range. In this embodiment the coupling element comprises a concave bottom portion, a threaded exterior cylindrical sidewall, and a flat top. This coupling element is locked into the hole by being screwed into position once the screw has been fully inserted, forming a flush external surface of the plate while locking the screw within the plate.

DETAILED DESCRIPTION OF THE PREFERRED EMBODIMENT

While the present invention will be described more fully hereinafter with reference to the accompanying drawings, in which particular embodiments and methods of fabrication are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 3:
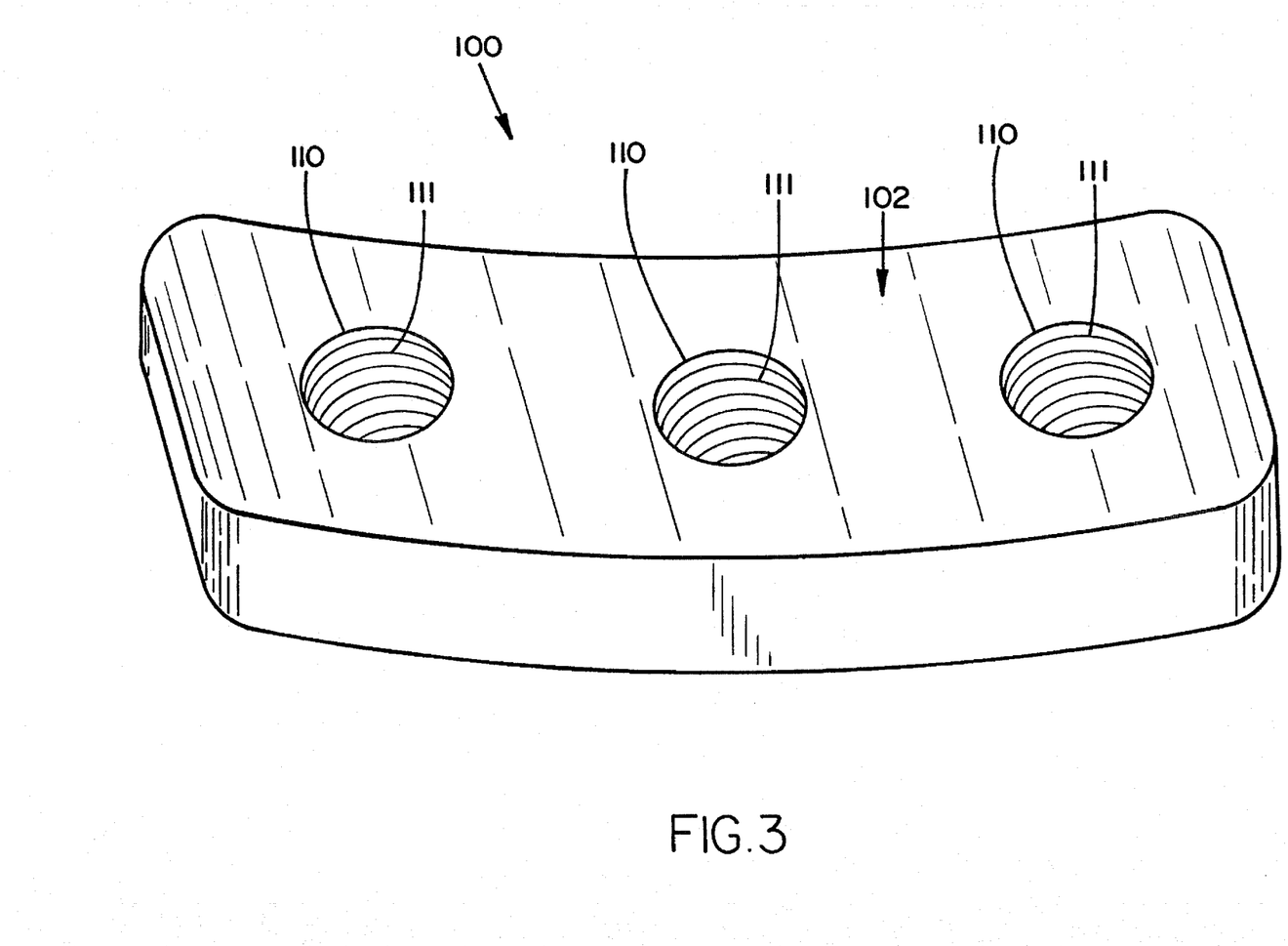
FIG. 3 is a perspective view of a locking lateral mass plate which is an element of one aspect of the present invention.

Referring now to FIG. 3 a plate which is an element of the present invention is shown in a perspective view. The plate 100 may be constructed of any suitably biocompatible material which has the structural strength and durability to withstand the cyclical loading associated with long term fixation to the spine. Materials which would be suitable for such applications include titanium alloys and steels. A specific titanium material which has been utilized in implants of the prior art include ASTM F-136 titanium alloy (Ti 6AL-4V). This material has enhanced mechanical properties including fatigue endurance and tensile strength, as compared with pure titanium.

The plate 100 comprises a narrow elongate planar body having a top surface 102 and a bottom surface (not shown). A slight positive curvature along the elongate axis is provided to the plate 100 so that it may grossly conform to the curvate morphology of the cervical spine to which it couples.

A plurality of through holes 110, having internal threading 111, and which extend from the upper surface 102 through the lower surface, are disposed in the plate 100. The holes may be entirely perpendicular to the plane of the plate, or preferably may be offset in the general direction which screw angulation is desired. For example, the holes may be provided with 10 to 30 degrees of lateral outward biasing angulation. Each of the holes 110 is ideally suited for receiving therethrough a bone screw for affixing the plate to the lateral mass of a cervical vertebral bone.

Figure 4:
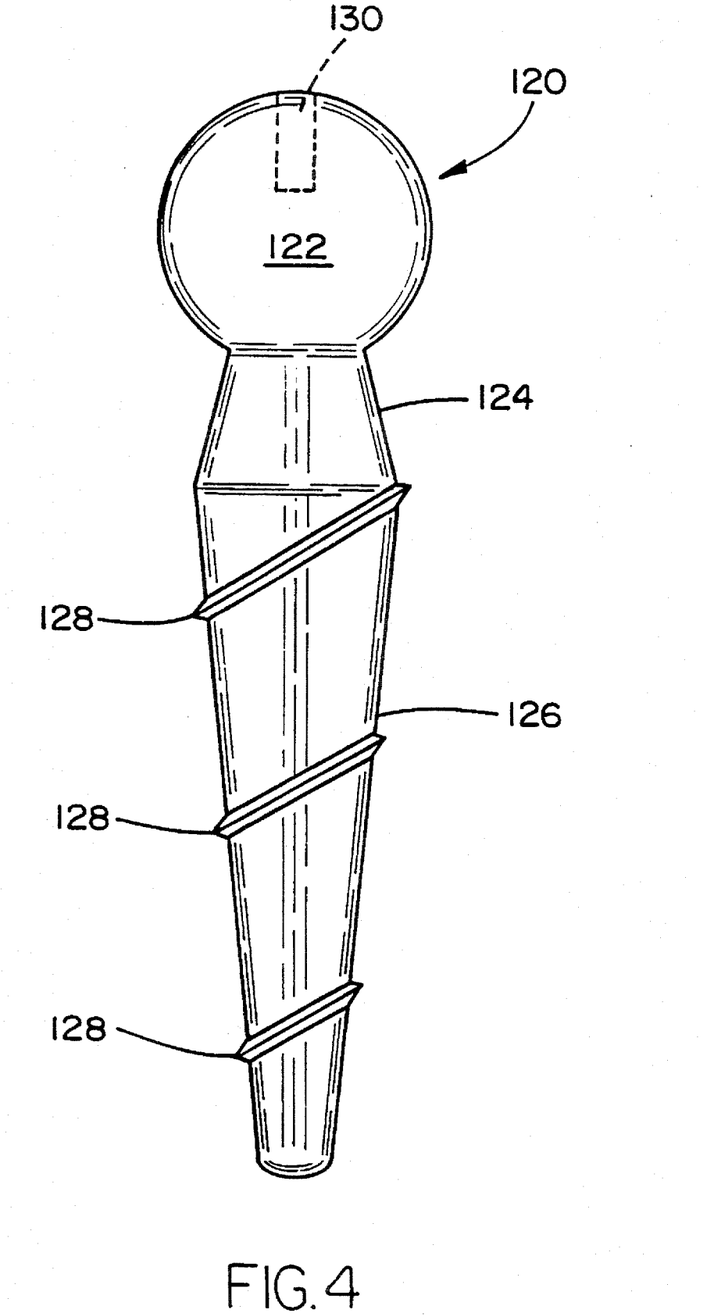
FIG. 4 is a perspective view of a bone screw which is an element of one aspect of the present invention.

Referring now also to FIG. 4, a screw of a type which is ideally suited for coupling the plate 100 to vertebral bones is shown in a side view. The screw 120 comprises a head portion 122, a neck 124, and a shaft 126. In FIG. 4, the shaft 126 is shown as having a tapered shape with a high pitch thread 128. It shall be understood that a variety of shaft designs are interchangeable with the present design. The specific choice of shaft features, such as thread pitch, or shaft diameter to thread diameter ratio, or overall shaft shape, etc. should be made by the physician with respect to the conditions of the patient's bone, however, this invention is compatible with a wide variety of shaft designs.

The head portion 122 of the screw 120 comprises a semi-spherical shape, which has a recess 130 in it. It is understood that the semi-spherical shape comprises a section of a sphere, greater in extent than a hemisphere, and exhibits an external contour which is equidistant from a center point within the head. In a preferred embodiment, the major cross-section of the semi-spherical head 122 (as shown in the two dimensional illustration of FIG. 4) includes at least 270 degrees of a circle.

The recess 130 defines a receiving locus for the application of a torque for driving the screw 120 into the bone. The specific shape of the recess 122 may be chosen to cooperate with any suitable screwdriving tool. For example, the recess 130 may comprise a slot for a flat-headed screwdriver, a crossed recess for a phillips head screwdriver, or most preferably, a hexagonally shaped hole for receiving an allen wrench. It is further preferable that the recess 130 be co-axial with the general elongate axis of the screw 120, and most particularly with respect to the shaft 126. Having the axes of the recess 130 and the shaft 126 co-linear facilitates the step of inserting the screw 120 into the bone.

The semi-spherical head portion 122 is connected to the shaft 126 at a neck portion 124. While it is preferable that the diameter of the shaft 126 be less than the radius of the semi-spherical head 122, it is also preferable that the neck 124 of the screw 120 be narrower than the widest portion of the shaft 126. This preferable dimension permits the screw to be inserted at a variety of angles while still permitting the coupling element (as described with respect to FIGS. 5a and 5b) to be screwed into the appropriate hole 110 of the plate 100.

Figure 5A:
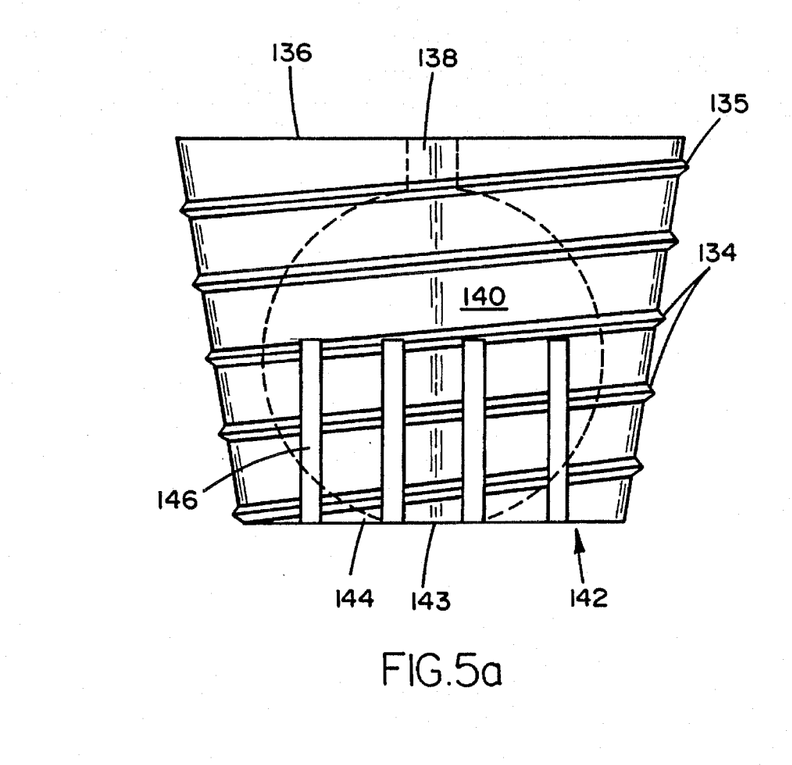
FIGS. 5a and 5b are perspective views of coupling elements which are aspects of embodiments of the present invention.
Figure 5B:
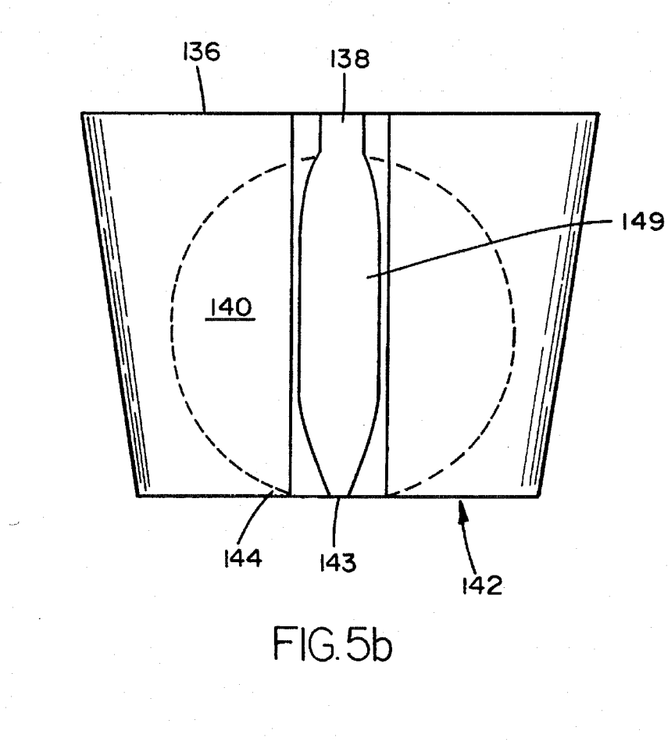

Referring now also to FIGS. 5a and 5b, two variations of the coupling element of the present invention are shown in side views, wherein phantom lines show the interior structure of the elements along a diametrical cross section. Each of the variations of the coupling element comprises a tapered cylindrical socket. The variation of FIG. 5a includes an external threading 134. This threading 134 and the diameter of the exterior of the cylinder is designed to mate with threading 111 of the holes 110 of the plate 100, so that the coupling element 132 may be screwed into the plate 100. It is preferable that the uppermost thread 135 be designed to crush-lock the coupling element into the hole 110. The variation shown in FIG. 5b does not include an external threading and is instead locked to the plate 100 via expansive pressure as described more fully below.

The top surface 136 of each variation of the coupling element, further comprises a through hole 138, which extends from the top surface 136 to an interior semi-spherical volume 140. This through hole 138 is designed such that the screwdriving tool which is used to insert the screw 120 into the bone may access and rotate the screw 120 through the coupling element.

Each variation further includes an interior semi-spherical volume 140 which is ideally suited for holding the head portion 122 of the screw 120, and permitting the screw to rotate through a range of angles. The coupling element 132 has a bottom 142 which has a circular hole (enumerated as 143 on the bottom surface of the side view of the coupling element) which forms the bottom entrance into the interior semi-spherical volume 140. It is understood that the head 122 of the screw 120 is held within the interior semi-spherical volume 140 by the annular rim, or support lip, 144 of the bottom 142 of the coupling element. This annular support lip 144 defines the circular opening 143 which has a diameter less than the diameter of the semi-spherical head 122 of the screw 120.

In the variation of this embodiment which is shown in FIG. 5a the lower portion of the coupling element 132 comprises slots 146 so that the physician may insert the head portion 122 into the interior volume 140. These slots 146 permit the lower portion of the coupling element 132 to expand to accept the inserted head portion 122. Insertion of the coupling elements into the through holes prevents the coupling elements from releasing the head 122 by preventing the circular opening 143 from expanding. In a highly preferred aspect of this variation, the holes 110 of the plate 100 and/or the coupling elements themselves are tapered inward with respect to insertion direction. In such an aspect, the step of screwing the coupling element 132 into the hole 110 causes the slots 146 to be compressed and, correspondingly, for the bottom entrance 143 and the annular lip 144 to lock the screw head into position.

Referring now to FIG. 5b, an alternative variation of the coupling element of this embodiment is shown in a side view, wherein phantom lines correspond to internal features of the coupling element taken along the diametric cross section. The significant differences between this variation and the coupling element of FIG. 5a are that this coupling element does not include an external threading or a plurality of slots in its lower portion. Rather includes a single axial slot 149 extending the entire length of the element. This slot interrupts the radial cross-section of the element, and extends from the elongate central axis to the cylindrical surface, therein rendering the element a ⅞ths ring. The head 122 of the screw can be inserted into the inner volume of the coupling element by expansion of the axial slot via application radial forces. Insertion of this variation of the coupling element into a hole (or if the element were not tapered, a tapered hole) provides a radial closing force to the slot, therein also causing the coupling element to lock to the screw head under expansion pressure.

Figure 6:
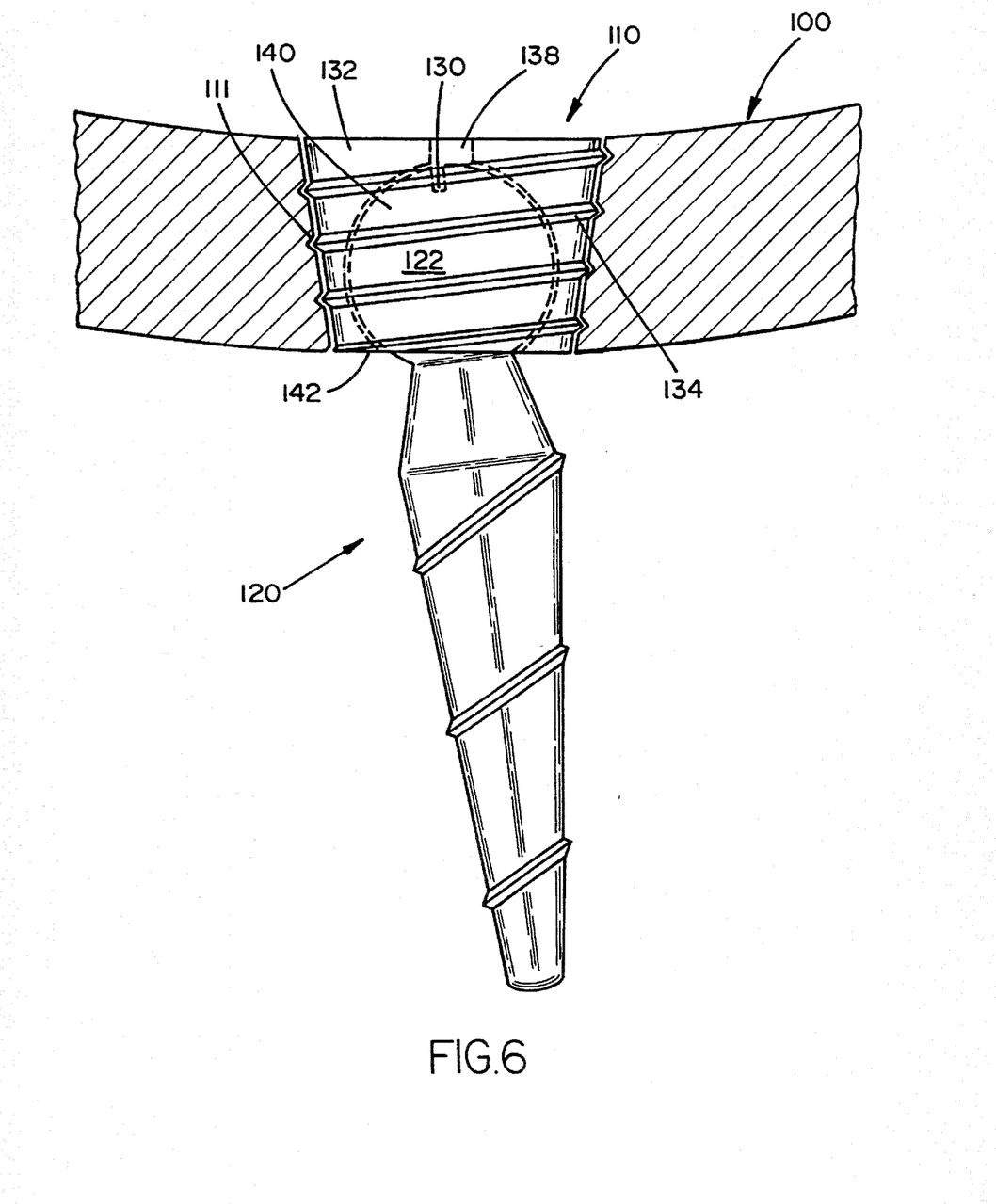
FIG. 6 is a side cross-sectional view of one embodiment of the present invention in a fully assembled form.

Referring now to FIG. 6, a cross sectional view of a fully assembled screw plate assembly of the present invention is shown. With reference to the relative positions of the screw 120, plate 100, and coupling element 132, the operative steps of implanting this screw plate assembly and affixing it to a pair of vertebral bones begins with preparing the bones through surgical tissue exposure and/or resection. Next the plate 100 is positioned against the bones and pre-drill holes are made into the lateral masses at the desired insertion angle for the screws 120. Each screw 120 and corresponding coupling element 132 are then placed together so that the head 122 is within the interior volume 140, whereby the two elements are able to rotate freely with respect to one another, but are nonetheless coupled.

The recess 130 in the screw 120 and the through hole 138 of the coupling element 132 are aligned at first, and an appropriate screwdriving tool is used to insert the screw 120 through the proper hole 110 or 112 and into the pre-drilled hole in the bone. Once the screw 120 has been screwed down to the point that the bottom surface of the coupling element 142 contacts the plate 100, the first threads 134 of the coupling element are mated to the threading 111 of the hole 110. Complete insertion of the coupling element 132 to the plate 100, locks the coupling element and screw to the plate, as well as locking the screw 120 and plate 100 to the bone.

Figure 7:
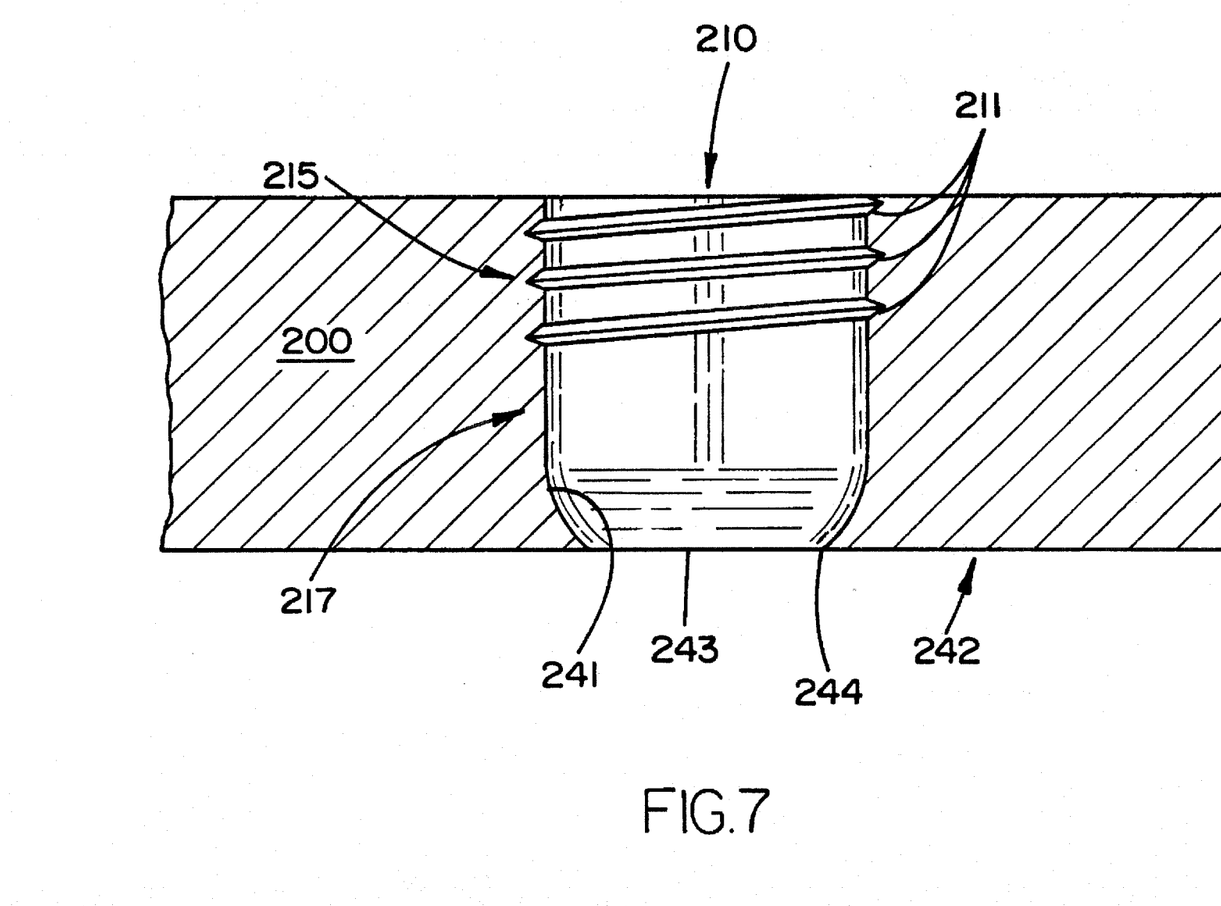
FIG. 7 is a side cross-sectional view of the plate of another embodiment of the present invention.

Referring now to FIGS. 4, 7, 8a, 8b, and 9, an alternative embodiment of the present invention is now described. Referring specifically to FIG. 7, a cross sectional view of a hole 210 in a plate 200, which is similar to the plate 100 of the first embodiment (shown in FIG. 3), is shown. The hole 210 is generally cylindrical and comprises an upper portion 215 and a lower portion 217. A threading 211 is provided in the upper portion 215. The lower portion 217 of the hole 210 is curved inward, the diameter of the hole decreases from the interface of the upper and lower portions of the plate 200 to the bottom 242.

Referring now also to FIG. 4, the curvature of the inner surface 241 of the lower portion of the hole 210 is set to match the semi-spherical head 122 of the screw 120. The bottom of the hole 243 is defined by an annular lip 244 which supports the screw 120 once it is inserted through the hole 210. The diameter of the bottom of the hole 243 is larger than the diameter of the neck 124 of the screw 120, but is less than the diameter of the head 122. This permits the screw 120 to be inserted at an angle through the plate, and into the bone. The maximum angle permitted is understood to be the angle at which the neck 124 of the screw 120 contacts the annular lip 244 of the plate 200.

Figure 8A:
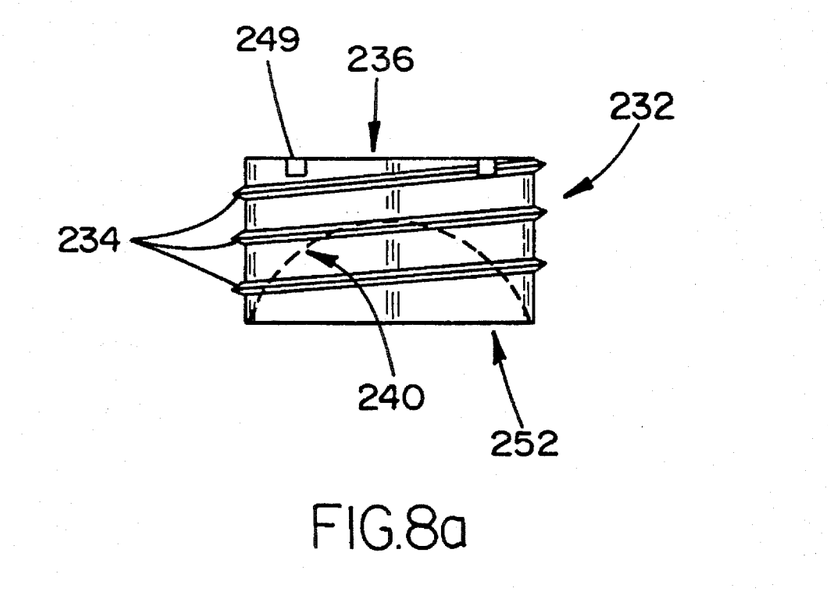
FIGS. 8a and 8b are side cross-sectional views of coupling elements of another embodiment of the present invention.
Figure 8B:
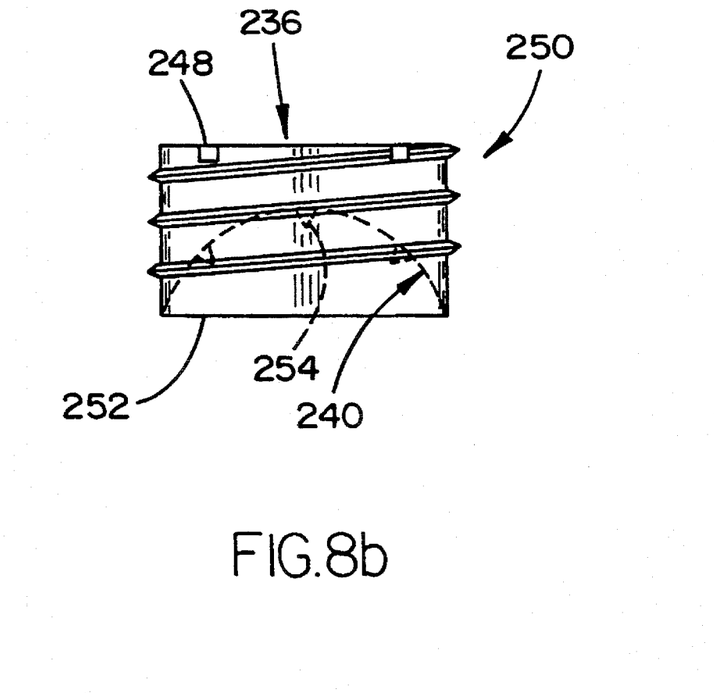

Referring now also to FIGS. 8a and 8b, alternative coupling elements 232 and 250, respectively, which are for locking the screw 120 to the plate 200, are provided in side views having phantom lines showing the diametric cross sectional features of each element. Specifically with respect to FIG. 8a, the coupling element 232 comprises a cylinder having threads 234 on its outside surface. The diameter and threads 234 of the element are chosen so that the element may be inserted into the appropriate hole 210 of the plate 200, and therewith form a flush external surface of the plate. The top surface 236 of the element includes suitable recesses 248 which mate with a screwdriving tool for insertion of the element 232 into the plate 200.

The bottom 252 of the coupling element comprises a concave semi-spherical surface 240. The radius of curvature of the concave surface 240 is preferably equivalent to the surface of the head portion 122 of the screw 120. This contour permits the flush insertion of the coupling element 232 into the hole 210, for the purposes of locking the screw to the plate and can upon sufficient application of force can lock the screw into a specific angulation.

Specifically referring to FIG. 8b, a coupling element 250 is shown in a side view having phantom lines corresponding to features of the element 250 along the diametric cross section. The concave semi-spherical surface 240 of this variation is provided with protuberances 254, for example small spikes or other grasping and locking means, which are capable of holding the head 122 of the screw 120 in a fixed angulation and locking the screw to the appropriate depth in a different manner.

Figure 9:
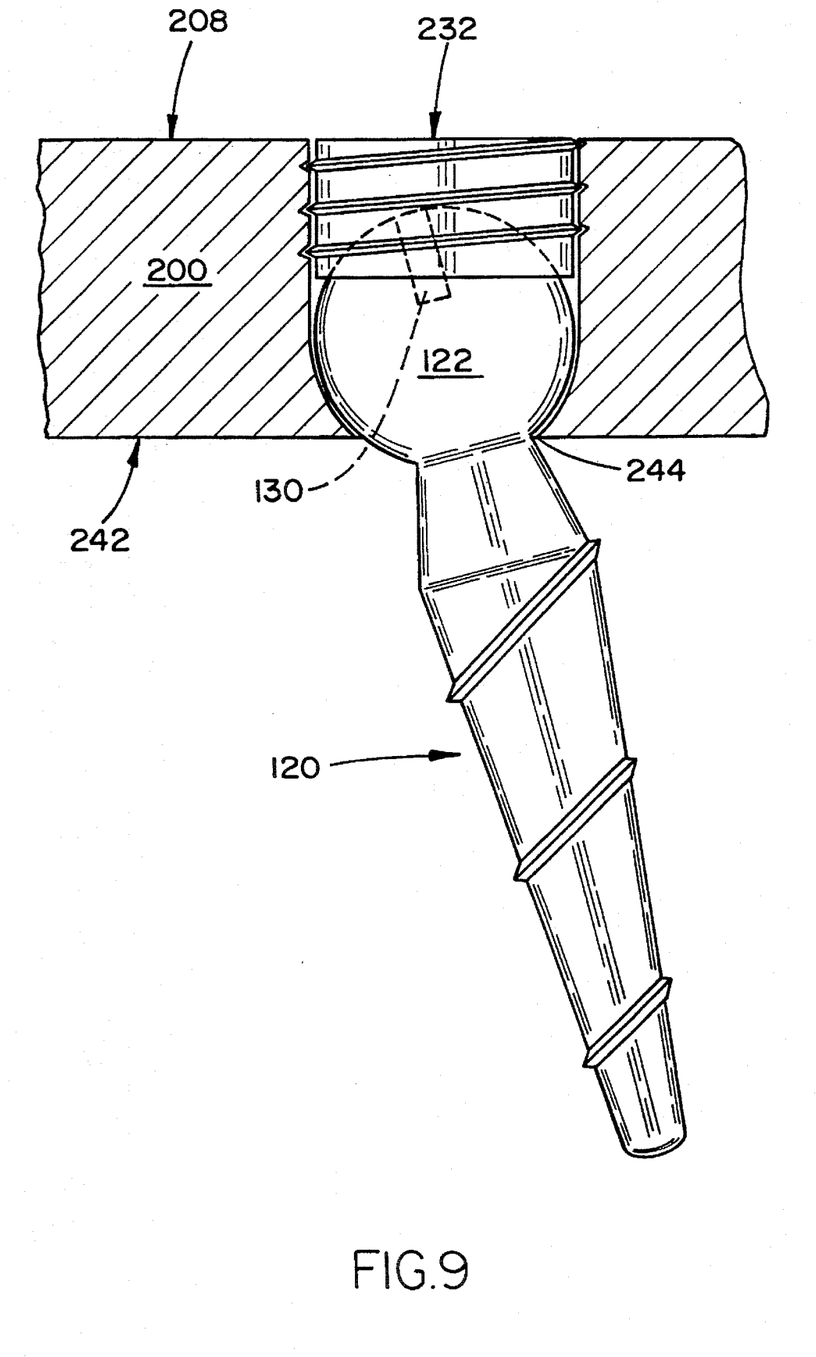
FIG. 9 is a side cross-sectional view of another embodiment of the present invention in a fully assembled form.

Referring now to FIG. 9, a side cross sectional view of a portion of the fully assembled embodiment of the present invention is shown. The operative sequence of steps for implantation of this device begins with the surgical exposition, final analysis, and preparation of the lateral masses. Once the appropriate decisions with respect to screw angulation and coupling variant have been made, the plate 200 is positioned across the exposed surfaces of the bones. Pre-drill holes are made into the bones at the desired angle, and the screws 120 are inserted with the use of a screwdriving tool mated to the recess 130 in the head 122. Once the screw 120 has been inserted, and the head 122 is properly supported by the annular lip 244 of the plate bottom 242, the coupling element 232 is screwed into the plate until the top portion of the coupling element is flush with the external surface 208 of the plate 200. In this position, the concave semi-spherical surface 240 of the bottom of the coupling element and the curved lower portion 241 of the hole 210 in the plate 200 define therebetween the volume in which the head 122 of the screw 120 is locked. As described above, it may be preferred that the surface of the head 122 of the screw 120 and the concave semi-spherical surface 240 of the coupling element 232 may lock together to fix the angle of the screw 120 with respect to the plate 200 once the coupling element 232 has been locked down.

While there has been described and illustrated implantation devices for stabilizing and immobilizing regions of the spine by affixing a polyaxial locking lateral masses screw plate assembly to the posterior portion of the cervical spine, it will be apparent to those skilled in the art that variations and modifications are possible without deviating from the broad spirit and principle of the present invention which shall be limited solely by the scope of the claims appended hereto.

We claim:

1. A polyaxial locking screw and plate assembly for the immobilization of vertebral bones, via fixation to posterior surfaces thereof, comprising:

an elongate plate having at least two through holes disposed in spaced relation with respect to each other along a longitudinal axis thereof;

a plurality of coupling elements, each having a semi-spherical interior volume, and each of said coupling elements being insertable into a corresponding through hole; and a plurality of bone screws, each of said bone screws having a semi-spherical head portion and a shaft, said shaft portion being insertable through the corresponding through hole and into the vertebral bone, and said semi-spherical head portion being rotationally freely mounted within the semi-spherical interior volume of the coupling element prior to insertion and such that the shaft of the bone screw and the coupling element may be inserted into a corresponding through hole and said shaft of the bone screw may be inserted into the lateral mass at a selected angle within a predetermined range of angles including non-perpendicular angles relative to the plate and thereby locking said coupling element and said semi-spherical head to said plate at said selected angle as said semi-spherical head and said coupling element are advanced into said corresponding through hole.

2. The polyaxial locking screw and plate assembly as set forth in claim 1, wherein each of said at least two through holes of said plate include an interior surface threading, and wherein each of said coupling elements includes an exterior surface threading which is matable to said interior surface threading, whereby each of said coupling elements is insertable into said corresponding through hole via engagement of said interior and exterior surface threadings.

3. The polyaxial locking screw and plate assembly as set forth in claim 1, wherein said interior semi-spherical volume is defined by a curved interior surface, which forms a receiving socket into which the semi-spherical portion head portion is inserted whereby the head portion of said screw is rotationally freely mounted in said coupling element.

4. The polyaxial locking screw and plate assembly as set forth in claim 3, wherein the curved interior surface of said coupling element further comprises at least one slot which permit the interior semi-spherical volume to expand thereby facilitating the insertion of said head portion of said screw therein.

5. The polyaxial locking screw and plate assembly as set forth in claim 4, wherein said at least one slot comprises a single slot which extends the axial length of the coupling element, therein defining the coupling element as an incomplete circular section.

6. The polyaxial locking screw and plate assembly as set forth in claim 4, wherein the corresponding through hole into which the coupling element is inserted is tapered inwardly, thereby causing, upon insertion of said coupling element into said corresponding through hole, the slots to be compressed, which causes the curved interior surface of the coupling element to lock the head portion of the screw at a definite insertion angle.

7. The polyaxial locking screw and plate assembly as set forth in claim 5, wherein the corresponding through hole into which the coupling element is inserted is tapered inwardly, thereby causing, upon insertion of said coupling element into said corresponding through hole, the single slot to compress together, and for said incomplete circular section to lock the head portion of the screw at a definite insertion angle.

\* \* \* \* \*